(12) United States Patent
Youngner

(10) Patent No.: US 7,589,329 B1
(45) Date of Patent: Sep. 15, 2009

(54) SYSTEMS AND METHODS FOR REMOTE OPTICAL SENSING

(75) Inventor: Daniel W. Youngner, Maple Grove, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/108,446

(22) Filed: Apr. 23, 2008

(51) Int. Cl.
*G01N 21/64* (2006.01)
(52) U.S. Cl. .................................................. 250/458.1
(58) Field of Classification Search .................. 313/502
See application file for complete search history.

(56) References Cited

U.S. PATENT DOCUMENTS

| | | | |
|---|---|---|---|
| 5,275,055 A | 1/1994 | Zook et al. | |
| 5,417,115 A | 5/1995 | Burns | |
| 5,559,358 A | 9/1996 | Burns et al. | |
| 6,246,638 B1 | 6/2001 | Zook et al. | |
| 6,710,355 B2 | 3/2004 | Youngner | |
| 6,714,007 B2 | 3/2004 | Youngner | |
| 6,917,751 B2 * | 7/2005 | Wang et al. | 385/147 |
| 2003/0137296 A1 | 7/2003 | Youngner | |
| 2003/0146393 A1 | 8/2003 | Youngner | |

\* cited by examiner

*Primary Examiner*—Constantine Hannaher
(74) *Attorney, Agent, or Firm*—Fogg & Powers LLC

(57) ABSTRACT

An optical-based sensor system that detects emitted light. An exemplary embodiment of an optical-based sensor has a substrate with a surface and an internal region; a shell disposed above the substrate surface, the shell operable to receive incident light characterized by a first wavelength; a beam disposed below the shell; a photodiode on the substrate surface below the beam, and in response to receiving a first portion of the incident light, the photodiode is operable to generate a charge such that a motion is induced to resonate at a resonate frequency; and a phosphor in the substrate internal region and operable to receive a second portion of the incident light, the phosphor further operable to emit light characterized by at least one second wavelength that is different from the first wavelength of the incident light, the phosphor emitted light transmitted through the photodiode, the beam, and the shell.

18 Claims, 3 Drawing Sheets

SYSTEMS AND METHODS FOR REMOTE OPTICAL SENSING

BACKGROUND OF THE INVENTION

Sometimes there is a need to sense a characteristic of an object of interest, such as, but not limited to, a temperature, a pressure, a strain, or the like, from a remote distance. For example, the object may be across a room or in a remote building. Further, it may be desirable to sense characteristics of an object that may be moving or that may be in different locations at different times.

In many such situations it is not possible to communicatively couple the sensing device to the object of interest by the use of wires, optic fibers, or RF links to make the sensing measurement. With an optical-based sensor, the sensing might be made by shining a beam of light onto the optical-based sensor and sensing the light reflected from the optical-based sensor. But if the optical-based sensor is very small, and/or if the distance between the optical-based sensor and the detecting sensor is great, the returning light reflected from the optical-based sensor may not be readily detectable and/or discernable if received. For example, the background scatter of light reflected from the optical-based sensor may be significant enough such that an insufficient amount of returning light is detectable by the detecting sensor. As another example, optical background noise from other light sources may interfere with and/or mask the reflected light signal such that the returning light reflected from the optical-based sensor becomes lost in the optical background noise generated by the other light sources.

An optically powered resonant integrated microstructure (O-RIMS) pressure sensor is operable to sense characteristics of an object of interest based upon detection of modulated light reflected from the O-RIMS optical-based sensor. An exemplary O-RIMS sensor is disclosed in U.S. Pat. No. 6,710,355, entitled "OPTICALLY POWERED RESONANT INTEGRATED MICROSTRUCTURE PRESSURE SENSOR" to Daniel W. Youngner, filed on Feb. 7, 2002, which is incorporated by reference herein in its entirety. Although this O-RIMS optical-based sensor may be suitable for detecting characteristics of an object of interest under a variety of conditions, it may not be a very effective optical-based sensor when the source of the light that is incident on the O-RIMS optical-based sensor is remote, and/or when the detecting sensor is remote from the O-RIMS optical-based sensor.

SUMMARY OF THE INVENTION

Systems and methods of remote sensing are disclosed. An exemplary embodiment has a substrate with a surface and an internal region with a shell disposed above the substrate surface, the shell operable to receive incident light emitted by a remote light source, the incident light characterized by at least one first wavelength; a beam disposed below the shell; a photodiode on the substrate surface below the beam, and in response to receiving a first portion of the incident light, the photodiode is operable to generate a charge that attracts the beam such that a motion is induced in the beam to cause the beam to resonate at a resonate frequency; and a phosphor in the substrate internal region and operable to receive a second portion of the incident light, the phosphor further operable to emit light characterized by at least one second wavelength that is different from the first wavelength of the incident light, the phosphor emitted light transmitted through the photodiode, the beam, and the shell. The phosphor-emitted light is partially reflected off of the beam so that a Fabry-Perot cavity is established involving the beam and either the substrate or the shell. As the beam moves up and down the Fabry-Perot cavity modulates the light that is emitted from the phosphor and that travels to the remote detector.

In accordance with further aspects, an exemplary embodiment receives incident light on an outer surface of a shell of the O-RIMS sensor, the incident light characterized by at least one first wavelength; transmits a first portion of the received incident light through the shell, through a beam, and onto a photodiode; in response to transmitting the first portion of the incident light onto the photodiode, generates a charge in the photodiode that attracts the beam such that a motion is induced in the beam to resonate at a resonate frequency; transmits a second portion of the received incident light onto a phosphor embedded in a substrate; and emits light from the phosphor in response to receiving the second portion of the received incident light, the phosphor emitted light characterized by at least one second wavelength.

BRIEF DESCRIPTION OF THE DRAWINGS

Preferred and alternative embodiments are described in detail below with reference to the following drawings.

DETAILED DESCRIPTION OF THE PREFERRED EMBODIMENT

Figure 1:
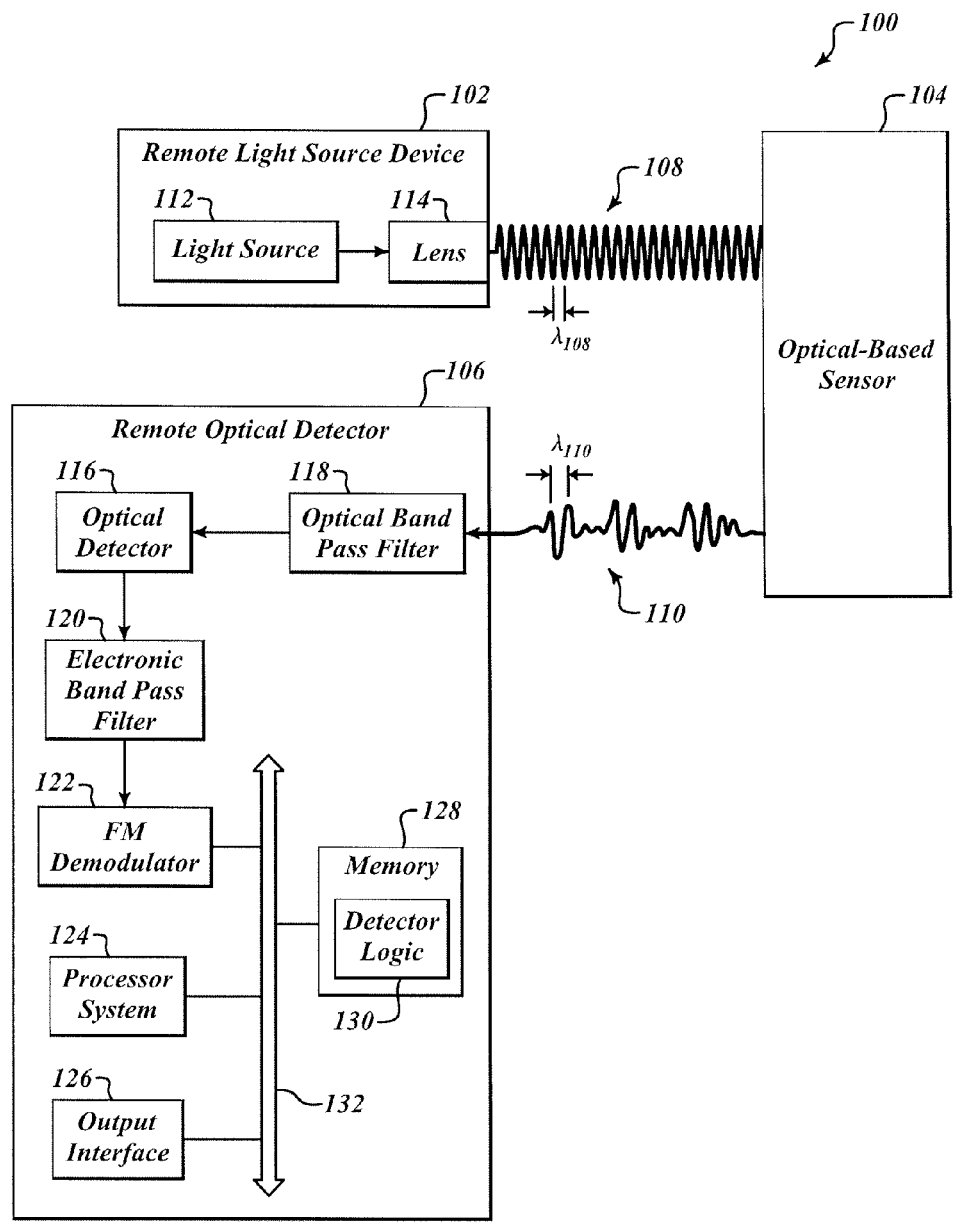
FIG. 1 is a block diagram of an embodiment of an optical-based sensor system.

FIG. 1 is a block diagram of an embodiment of an optical-based sensor system 100. The optical-based sensor system 100 comprises a remote light source device 102, an optical-based sensor 104, and a remote optical detector 106.

The remote light source device 102 emits light 108, comprising a first wavelength, towards the optical-based sensor 104. In response to receiving the light 108, the optical-based sensor 104 emits the modulated light 110. The modulated light 110 is modulated by phenomena that affect the optical-based sensor 104. The emitted modulated light 110 comprises a second wavelength that is substantially different from the first wavelength of the light 108. The remote optical detector 106 is operable to remotely detect the modulated light 110 emitted from the optical-based sensor 104.

The light 108 and/or the modulated light 110 may have one or more wavelengths ($\lambda_{108}$, $\lambda_{110}$) that are within and/or outside of the range of visible light, such as, but not limited to, near-infrared frequency light. Further, the light 108 and/or the modulated light 110 may be characterized by a wavelength range.

The remote light source device 102 comprises a light source 112 and an optional lens 114. The light source 112 may be any suitable source of light that emits light that is receivable from a distance by the optical-based sensor system 100. For example, the remote light source device 102 may be located many yards away, or even many miles away, from the optical-based sensor 104.

Preferably, the light 108 is emitted as a beam directed towards and onto the optical-based sensor 104 by a user. In one embodiment, the light source 112 is a laser. The laser emits a beam of light at a particular wavelength, or any of a range of wavelengths. The light 108 is preferably of a frequency that is transmissive through the shell 208, the beam 210, photodiode 212, and/or the substrate 202. For example, but not limited to, the light source 112 may emit light at a wavelength corresponding to near-infrared or infrared (IR) light. In other embodiments, the light source 112 may emit light of any of a broad range of wavelengths. In some embodiments, the light source 112 emits collimated light that may be more efficiently directed towards the optical-based sensor 104.

The optional lens 114 may be used to adjust characteristics of the light 108 emitted by the light source 112. In one embodiment, the lens 114 may be a filter that is transmissive of a particular wavelength, or wavelength range. For example, but not limited to, the lens 114 may pass a wavelength of light corresponding to near-infrared or infrared (IR) light. Alternatively, or additionally, the lens 114 may be operable to focus, collimate, or otherwise condition the light emitted by the light source 112.

The remote optical detector 106 comprises an optical detector 116, an optional optical band pass filter 118, an optional electronic band pass filter 120, an optional frequency modulation (FM) demodulator 122, an optional processor system 124, an optional output interface 126, and an optional memory 128. The detector logic 130 resides in the memory 128. In an exemplary embodiment of the remote optical detector 106, the selected ones of the above components may be communicatively coupled to each other via a communication bus 132. Some embodiments may include one of, or both of, the optical band pass filter 118 and the electronic band pass filter 120.

The optical detector 116 is operable to receive the modulated light 110 emitted by the optical-based sensor 104. In a preferred embodiment, the optical band pass filter 118 receives and processes the modulated light 110. In an exemplary embodiment, the optical band pass filter 118 is configured as a relatively narrow band pass filter having a band pass frequency corresponding to the frequency of the modulated light 110.

The optical detector 116 generates a signal with information corresponding to the detected modulated light 110. In some embodiments, an optional electronic band pass filter 120 may be included that further filters the electronic signal output from the optical detector 116. The FM demodulator 122 demodulates the electronic signal to retrieve the information from the carrier portion of the signal 110. Further, some embodiments may have the optical detector 116 configured to output a digital signal.

A processor system 124 processes the information in the signal based upon the intended functionality of the optical-based sensor system 100. For example, the optical-based sensor system 100 may be configured to determine information of interest that is related to a characteristic that is detectable by the optical-based sensor 104, such as, but not limited to, a temperature, a pressure, a strain, or the like.

The determined information of interest is output to a user in a meaningful manner by the output interface 126 that is in communication with a presentation device or system (not shown). For example, the output interface 126 may provide information to a speaker, a display, a printing device, another processing system, and/or another memory. The remote optical detector 106 may include a memory 128 with detector logic 130 residing therein. Thus, the processor system 124 may retrieve the detector logic 130 so that the signal generated by the optical detector 116 can be processed to determine the information of interest residing in the signal output by the optical detector 116.

The above-described components of the remote optical detector 106 may be communicatively coupled to each other via the communication bus 132, thereby providing connectivity between the above-described components. In alternative embodiments, the above-described components may be connectively coupled to each other in a different manner than illustrated in FIG. 1. For example, one or more of the above-described components may be directly coupled to the processor system 124 or may be coupled to the processor system 124 via intermediary components (not shown).

Figure 2:
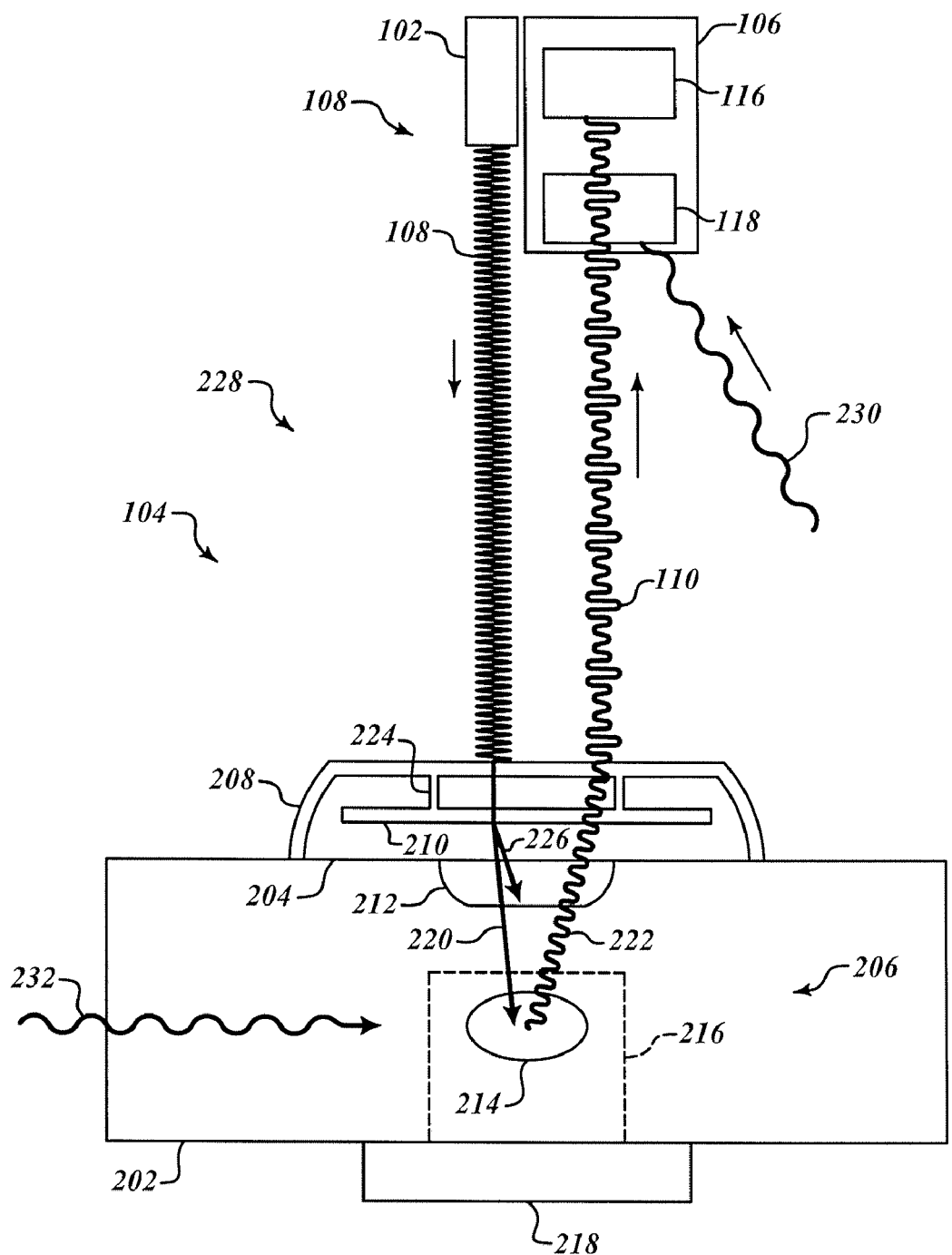
FIG. 2 is a block diagram of an embodiment of an optical-based sensor receiving light emitted from a remote light source device and transmitting light to a remote optical detector.

FIG. 2 is a block diagram of an embodiment of an optical-based sensor 104 receiving light 108 emitted from the remote light source device 102 and transmitting the modulated light 110 to the remote optical detector 106. The optical-based sensor 104 comprises a substrate 202 with a surface 204 and an internal region 206, a shell 208 disposed above the substrate surface 204, a beam 210 disposed below the shell 208, a photodiode 212 on the substrate surface 204 below the beam 210, and a phosphor 214 in the substrate internal region 206. In an exemplary embodiment, the phosphor 214 resides in a cavity 216 formed in the substrate internal region 206. A cover 218 may be used to seal the cavity 216 to retain the phosphor 214.

A portion 220 of the light 108 incident on the shell 208 is transmitted through the shell 208, the beam 210, and the photodiode 212. The phosphor 214 is operable to receive the portion 220 of the incident light 108. In response to the phosphor 214 receiving the portion 220 of the light 108, the phosphor 214 becomes excited and emits an amount of phosphor emitted light 222. The phosphor emitted light 222 is characterized by at least one wavelength or a wavelength range. The wavelength of the phosphor emitted light 222 is preferably different from the wavelength of the received light 108. Preferably, the phosphor emitted light 222 is a red-shifted wavelength of the incident light 108.

The phosphor emitted light 222 is optionally transmitted through and/or around the photodiode 212, then is transmitted through the beam 210 and the shell 208. In an exemplary embodiment, the phosphor 214 is neodymium trishydroxyquinoline. Other embodiments use other types of chemicals for the phosphor 214.

The optical-based sensor 104 has its beam 210, a microbeam having a resonant frequency, held by supports 224. The resonant frequency of the beam 210 is a function of its design characteristics, and is variable in response to flexure of the beam 210. The beam 210 may be vacuum encapsulated by the shell 208, which may be a polysilicon material. The shell 208 and the beam 210 together form a micromachined integrated device.

As noted above, a portion 226 of the light 108 passes through the shell 208, through the beam 210, and onto the photodiode 212 situated beneath the beam 210. The portion 226 of the light 108 incident on the photodiode 212 generates a charge in the photodiode 212. The generated charge creates an electrostatic attraction between the beam 210 and the photodiode 212. When the incident light 108 ceases (or decreases in magnitude), the attraction of the beam ends (or decreases). As the incident light 108 beats at a predefined frequency, the beam 210 is excited into resonance. In one embodiment, the predefined frequency of the incident light 108 established by modulating the external light source 102 using phase-locking techniques. In other embodiments, conditions for self-resonance may be created as described in U.S. Pat. No. 6,710,355.

The beam 210, the substrate 202, and the shell 208 form a Fabry-Perot cavity. Accordingly, the phosphor emitted light 222 is modulated by the beam 210, thus generating the modulated light 110. The modulated light 110 exits the shell 208 and enters the free space 228, creating an optical signal whose intensity is modulated (changes) as the beam 210 vibrates. The beat frequency induced in phosphor emitted light 222 corresponds to the frequency of vibration of the beam 210.

Accordingly, when the modulated light 110 is received by the remote optical detector 106, the modulated light 110 may be evaluated to determine the vibratory frequency of the beam 210. Since physical characteristics of the beam 210 are modified by the parameter sensed by the optical-based sensor 104, the resonant vibratory frequency of the beam 210 changes. As the vibratory frequency of the beam 210 changes, the modulation of the modulated light 110 changes. The frequency of the modulated light 110 is detectable by the remote optical detector 106.

Embodiments of the optical-based sensor system 100 may be particularly useful in cases where a significant amount of background light 230 is present. As long as the intensity of the modulated light 110 is comparable to or greater than the intensity of the background light 230 having the same frequency as the modulated light 110, there is a net gain in the signal-to-noise ratio. For example, the walls of a room lit with an incandescent light bulb might emit approximately $1 \times 10^{-8}$ $W/cm^2$ of light in the frequency range of the phosphor emitted light 222. By contrast, the phosphor 214 may be operable to emit $1 \times 10^{-5}$ $W/cm^2$ in the same wavelength band. In this example, a factor of 1000 improvement in the signal-to-noise ratio is achieved by using the optical-based sensor system 100.

Embodiments of the optical-based sensor system 100 are also particularly useful when there is significant reflection of the illuminating light 108 back toward the remote optical detector 106. As an example, consider the case in which the reflected light is 1000× more intense than the modulated information-carrying light 110. By filtering out the reflected light while allowing modulated light 110 to pass, a factor of 1000× improvement in signal to noise (S/N) ratio would be achieved. In the most general case, there is both reflected illuminating light 108 and background light 230. This invention improves the S/N ratio for both cases.

Figure 3:
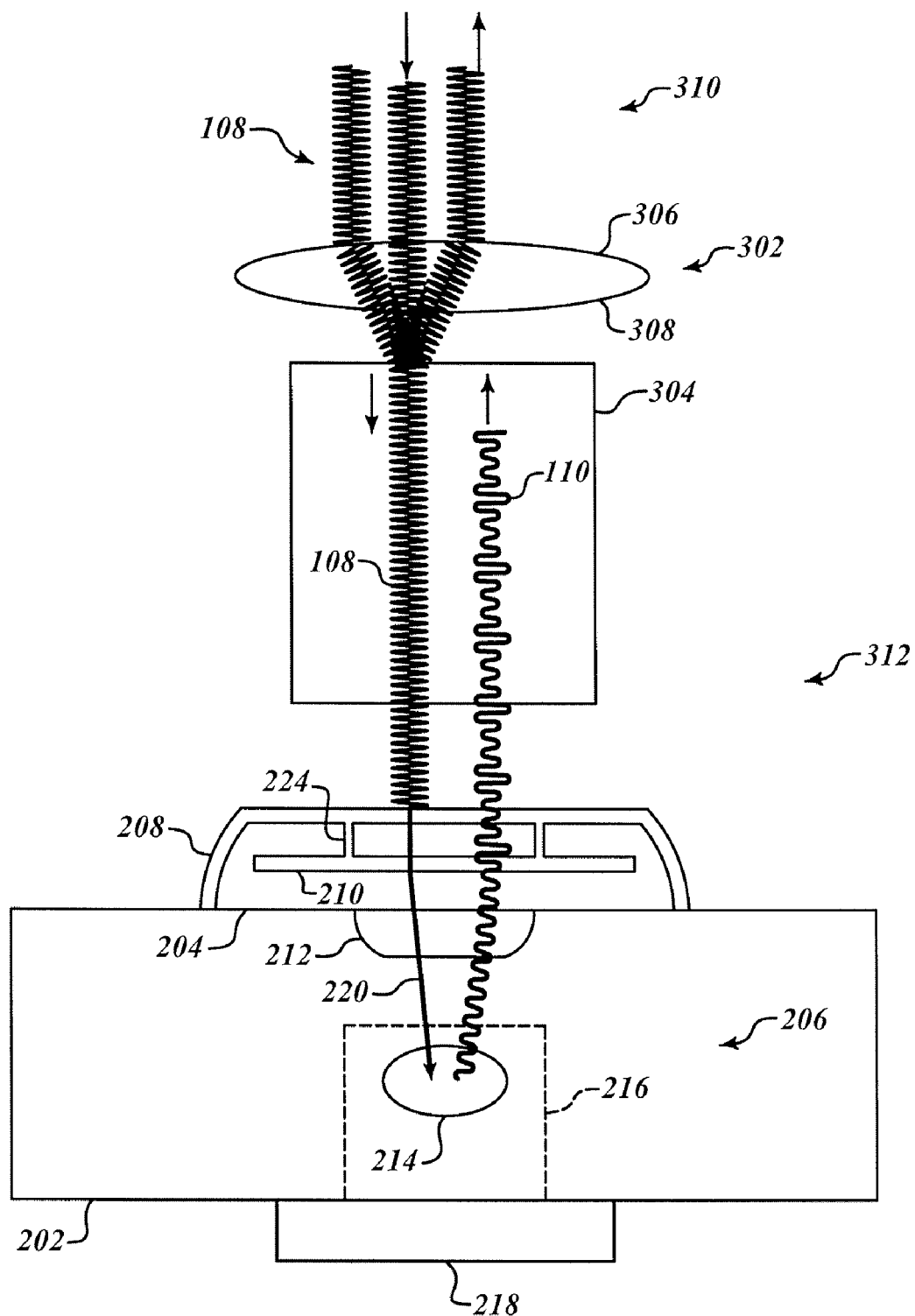
FIG. 3 is a block diagram of an alternative embodiment of an optical-based sensor.

FIG. 3 is a block diagram of portions of an alternative embodiment of an optical-based sensor system 100. Included are a collimating lens 302 and an optical fiber 304. The collimating lens 302 and the optical fiber 304, which may be used separately or used in cooperation with each other, condition the light 108 emitted by the remote light source device 102 and the modulated light 110 emitted by the phosphor 214 and modulated by the beam 210.

The collimating lens 302 may be used to gather the light 108 emitted by the light source 112 at its exterior surface 306. In one embodiment, the collimating lens 302 may be a filter that is transmissive of a particular wavelength, or wavelength range. For example, but not limited to, the collimating lens 302 may pass a wavelength of light corresponding to the near-infrared wavelength. Alternatively, or additionally, the collimating lens 302 may be operable to focus, collimate, or otherwise condition the incident light 108. The light exits from the surface 308.

The optical fiber 304 may be used to communicate the light 108 from a first location 310 where the light 108 is received to a second location 312 proximate to the surface of the shell 208. The optical fiber 304 may be advantageous in applications where the optical-based acoustic sensor 104 is located at a position where light 108 can not be readily directed onto the shell 208 of the optical-based acoustic sensor 104 and/or where the phosphor emitted light 226 can not be readily directed towards the remote optical detector 106.

For example, the optical-based sensor 104 may be located on one side of a corner of a structure (e.g.; a wall) that is not in the line of sight of the remote light source device 102. Accordingly, the collimating lens 302, if used, directs the light 108 into the optical fiber 304. The optical fiber 304 directs the light 108 around the corner and then emits the light 108 such that the light 108 becomes incident on the shell 108. The optical fiber 304 then receives the phosphor modulated light 110, directs the modulated light 110 back around the corner, and then emits the modulated light 110 such that the modulated light 110 is detectable by the optical detector 116.

In a preferred embodiment, the remote light source device 102 and the remote optical detector 106 may be incorporated into a single device. One embodiment may be configured similar to a gun such that the light 108, when emitted as a beam of light, may be directed towards and onto the optical-based sensor 104 by a user. By incorporating the remote light source device 102 and the remote optical detector 106 into a single device, the remote optical detector 106 would also be oriented the same as the remote light source device 102. Accordingly, the remote optical detector 106 would also be directed towards the optical-based sensor 104. Thus, a laser light source is pointable at the optical optical-based sensor 104 from a remote distance. In some embodiments, the lens 114 (FIG. 1) may be also used to receive the modulated light 110 emitted from the optical-based sensor 104.

In alternative embodiments, the remote light source device 102 and the remote optical detector 106 are separated. In such embodiments, the light 108 emitted by the light source device 102 need not pass through the shell 208, the beam 210, and/or the photodiode 212, to become incident on the phosphor 214. For example, the light source device 102 may be located to the side of the substrate 202 such that a portion 232 of the emitted light 108 passes through the substrate 202 and onto the phosphor 214.

As noted above, in some situations it may be desirable to monitor characteristics of a moving object. Since embodiments of the optical-based sensor 104 do not require a power source or connectors to transmit detected sounds, the optical-based sensor 104 may be located on the moving object. The mounting of the optical-based sensor 104 on an object of interest may be covert.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The invention claimed is:

1. An optical sensor, comprising:
   a substrate with a surface and an internal region;
   a shell disposed above the substrate surface, the shell operable to receive incident light emitted by a remote light source, the incident light characterized by at least one first wavelength;
   a beam disposed below the shell;
   a photodiode on the substrate surface below the beam, which photodiode, in response to receiving a first portion of the incident light, is operable to generate a charge on the beam such that a motion is induced in the beam to cause the beam to resonate; and
   a phosphor embedded in the substrate internal region below the photodiode and operable to receive a second portion of the incident light, the phosphor being further operable to emit light characterized by at least one second wavelength that is different from the first wavelength of the incident light, the phosphor emitted light being transmitted through the photodiode, the beam, and the shell.

2. The optical sensor of claim 1, wherein the first wavelength of the incident light corresponds to a substantially near-infrared light wavelength.

3. The optical sensor of claim 1, wherein the second wavelength of the phosphor emitted light corresponds to a substantially red-shifted wavelength of light.

4. The optical sensor of claim 1, wherein the beam is affixed to an inner surface of the shell.

5. The optical sensor of claim 4, wherein the beam is affixed to the inner surface of the shell by two posts.

6. The optical sensor of claim 1, further comprising:
a collimating lens with an external surface and an interior surface, the collimating lens disposed above the shell and operable to collect the incident light over the exterior surface, operable to collimate the collected incident light, and operable to transmit the incident light from the interior surface; and
an optical fiber disposed between collimating lens and the shell, the optical fiber operable to receive the incident light from the interior surface of the collimating lens and operable to transmit the incident light to the outer surface of the shell.

7. A method for emitting light from an optically powered resonant integrated microstructure (O-RIMS) sensor, comprising:
receiving incident light on an outer surface of a shell of the O-RIMS sensor, the incident light characterized by at least one first wavelength;
transmitting a first portion of the received incident light through the shell, through a beam, and onto a photodiode;
in response to transmitting the first portion of the incident light onto the photodiode, generating a charge in the photodiode that attracts the beam such that a motion is induced in the beam to resonate at a resonant frequency;
transmitting a second portion of the received incident light onto a phosphor embedded in a substrate; and
emitting light from the phosphor in response to receiving the second portion of the received incident light, the phosphor emitted light characterized by at least one second wavelength.

8. The method of claim 7, further comprising:
transmitting the phosphor emitted light through the photodiode, through the beam, and through the shell such that the phosphor emitted light is emitted from the outer surface of the shell of the O-RIMS sensor.

9. The method of claim 8, further comprising:
modulating at least one characteristic of the phosphor emitted light by the resonate motion of the beam.

10. The method of claim 9, wherein the at least one modulated characteristic of the phosphor emitted light transmitted is an amplitude.

11. The method of claim 8, further comprising:
modulating the resonate motion of the beam at a first resonate frequency, wherein the at least one modulated characteristic of the phosphor emitted light transmitted from the outer surface of the shell of the O-RIMS sensor corresponds to the first resonate frequency;
inducing strain in the beam, the strain corresponding to a sensed parameter sensed by the O-RIMS sensor; and
in response to inducing the strain in the beam, modulating the resonate motion of the beam at a second resonate frequency, wherein the at least one modulated characteristic of the phosphor emitted light transmitted from the outer surface of the shell of the O-RIMS sensor corresponds to the second resonate frequency.

12. The method of claim 8, wherein transmitting the second portion of the received incident light comprises:
transmitting the second portion of the received incident light through the shell, the beam, and the photodiode.

13. An optical-based sensor system, comprising:
an optical sensor, the optical sensor comprising:
a substrate with a surface and an internal region;
a shell disposed above the substrate surface, the shell operable to receive incident light emitted by a remote light source, the incident light characterized by at least one first wavelength;
a beam affixed to an inner surface of the shell;
a photodiode on the substrate surface below the beam, and in response to receiving a first portion of the incident light, the photodiode is operable to generate a charge that attracts the beam such that a motion is induced in the beam to cause the beam to resonate at a resonant frequency; and
a phosphor embedded in the substrate internal region and surrounded by the substrate, the phosphor operable to receive a second portion of the incident light and operable to emit light characterized by at least one second wavelength that is different from the first wavelength of the incident light, the phosphor emitted light transmitted through the photodiode, the beam, and the shell;
a remote light source operable to emit the incident light onto an outer surface of the shell; and
a remote optical detector that is sensitive to the at least one second wavelength of the phosphor emitted light, and is further operable to generate a signal having information corresponding to a characteristic of the received phosphor emitted light.

14. The optical-based sensor system of claim 13, further comprising:
a collimating lens with a first surface and a second surface, the collimating lens disposed above the shell and operable to collect the incident light over the first surface, operable to collimate the collected incident beam of light, and operable to transmit the incident beam of light from the second surface.

15. The optical-based sensor system of claim 14, further comprising:
an optical fiber disposed between the collimating lens and the shell, the optical fiber operable to receive the incident light from the collimating lens and operable to transit the incident light to the outer surface of the shell.

16. The optical-based sensor system of claim 13, wherein the remote optical detector comprises:
a band pass filter operable to pass light having the second wavelength such that the received phosphor emitted light is passed through the band pass filter, and further operable to block light having other frequencies such that a signal to noise ratio of the detected phosphor emitted light is increased.

17. The optical-based sensor system of claim 13, wherein the remote light source comprises:
a laser operable to generate a focused beam of light having the first wavelength, such that the laser is pointable at the optical sensor from a remote distance.

18. The optical-based sensor system of claim 13 wherein the second portion of the incident light is transmitted through at least the shell and the beam.

* * * * *